United States Patent [19]

Iacobucci et al.

[11] Patent Number: 4,788,069
[45] Date of Patent: Nov. 29, 1988

[54] INTENSELY SWEET L-ASPARTYL-3-(BICYCLOALKYL)-L-ALANINE ALKYL ESTERS

[75] Inventors: Guillermo A. Iacobucci; James G. Sweeney; James G. King, III, all of Atlanta, Ga.

[73] Assignee: The Coca-Cola Company, Atlanta, Ga.

[21] Appl. No.: 32,129

[22] Filed: Mar. 27, 1987

[51] Int. Cl.$^4$ .................... C07K 5/06; A23L 1/236
[52] U.S. Cl. .................................. 426/548; 560/118
[58] Field of Search .................... 560/118; 426/548

[56] References Cited

U.S. PATENT DOCUMENTS

| | | | |
|---|---|---|---|
| 3,907,766 | 9/1975 | Fujino et al. | 260/112.5 |
| 3,959,245 | 5/1976 | Nakajima et al. | 260/112.5 |
| 3,978,034 | 8/1976 | Sheehan et al. | 260/112.5 |
| 4,571,308 | 2/1986 | Zanno et al. | 260/112.5 |
| 4,572,799 | 2/1986 | Zanno et al. | 260/112.5 |
| 4,603,012 | 7/1986 | Zanno et al. | 260/112.5 |
| 4,622,232 | 11/1986 | Zanno et al. | 426/548 |
| 4,622,417 | 11/1986 | Barnett et al. | 560/118 |
| 4,622,418 | 11/1986 | Barnett et al. | 560/118 |
| 4,626,442 | 12/1986 | Zanno et al. | 426/548 |
| 4,633,006 | 12/1986 | Barnett et al. | 560/1 |
| 4,634,792 | 1/1987 | Zanno et al. | 560/169 |
| 4,636,396 | 1/1987 | Zanno et al. | 426/548 |
| 4,638,071 | 1/1987 | Barnett et al. | 560/118 |

FOREIGN PATENT DOCUMENTS

| | | |
|---|---|---|
| 0168112 | 1/1986 | European Pat. Off. . |
| 0168882 | 1/1986 | European Pat. Off. . |
| 1229265 | 12/1972 | United Kingdom . |
| 1327560 | 8/1973 | United Kingdom . |

OTHER PUBLICATIONS

Mazur et al., U.S. "Structure–Taste Relationships of Some Dipeptides," J. American Chem. Soc., 91(10):2684–2691 (1969).
Iwamura, "Structure–Sweetness Relationshps of L-Aspartyl Dipeptide Analogues, A Receptor Site Topology," J. Med. Chem., 24:572–583 (1981).
Brussel et al., "Structure–Taste Relationship of Some Sweet-Tasting Dipeptide Esters," Z. Lebensmittel Unters.-Forsch., 159:337–343 (Bergmann, Munich, 1975).
Miyashita et al., "Structure–Taste Correlation of L Asaprtyl Dipeptides Using SIMCA Method," J. Med. Chem., 29:906–912 (1986).
Tsang et al., "Peptide Sweeteners 6, Structural Studies on the C-Terminal Amino Acid of L-Aspartyl Dipeptide Sweeteners," J. Med. Chem., 27:1663–1668 (1984).
Mazur et al., "Synthetic Sweeteners, 3-Aspartyl Dipeptide Esters from 1- and D-Alkylglycines," J. Med. Chem., 16(11):1284–1287 (1973).
Grosch et al., "Sussstoffe-struktur und Geschmack," Naturwissenschafte, 64(6):335–336 (Springer-Verlag, 1977).
Liu et al., "The Relationship Between the Structure and Sweetness of Aspartic Acid Depeptides," Sino–Amer. Symp. Chem. Nat. Prod. Proc. Beijing, 1980 (Science Press, 1982), pp. 254–256.
Fujino et al., "Structure–Taste Relationships of L—Aspartyl-Aminoalonic Acid Diesters," Chem. Pharm. Bul., 24(9):2112–2117 (1976).
Fujino et al., "L-Aspartyl-Aminoalonic Diesters," Die Naturwissenschaffen, Heft 7, S.351 (Springer-Verlag, 1973).

Primary Examiner—Michael L. Shippen
Attorney, Agent, or Firm—Kenyon & Kenyon

[57] ABSTRACT

The present invention relates to L-aspartyl-3-(bicycloalkyl)-L-alanine alkyl esters having high sweetness intensity, of the formula:

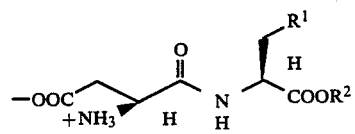

wherein $R^1$ is a substituted or an unsubstituted bicycloalkyl ring, said ring having 7 to 8 carbon atoms, the 2-position ring carbon atom is bound to the alamine moiety, the two carbon atoms of the ring that are vicinal to the 2-position carbon are each substituted by a hydrogen or lower alkyl, the total number of alkyl groups bound to the vicinal carbons is less than three, and $R^2$ is methyl. The "2R" configuration enantiomers of the $R^1$ group are especially preferred. In preferred embodiments of the invention, $R^1$ is a bornyl, camphanyl, norbornyl, 1-methylnorbornyl, 3-methylnorbornyl, 7,7-dimethylnorbornyl, bicyclo [2.2.2] octyl, or pinanyl ring. The compounds of the invention, or edible salts thereof, can be used for sweetening edible products such as foods and beverages.

22 Claims, No Drawings

INTENSELY SWEET L-ASPARTYL-3-(BICYCLOALKYL)-L-ALANINE ALKYL ESTERS

BACKGROUND OF THE INVENTION

The sweetener L-aspartyl-L-phenylalanine methyl ester (Formula 1) is known to be about 180 times sweeter than sucrose, weight to weight. Other peptides with increased sweetening power are also known to the art. See, for example, R. H. Mazur et al., *J. Am. Chem. Soc.* 91:2684–2691 (1969); Zanno et al., U.S. Pat. Nos. 4,572,799; Zanno et al., 4,571,308; Zanno et al., 4,603,012; H. Iwamura, *J. Med. Chem.* 24:572–583 (1981); L. B. P. Brussel et al., *Z. Lebensm. Untersuch.-Forsch.* 159:337–343 (1975); Y. Miyashita et al., *J. Med. Chem.* 29:906–912 (1986); Tsang et al., *J. Med. Chem.* 27:1663–1668 (1984); R. H. Mazur et al., *J. Med. Chem.* 16:1284 (1973); W. Grosch et al., *Naturwissenschaften* 64:335 (1977); Sheehan et al., U.S. Pat. No. 3,978,034.

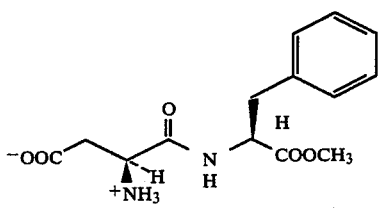

One compound discovered as a result of the research for high intensity sweeteners is L-aspartyl-2-amino malonyl methyl fenchyl diester, which has a fenchyl ester substituent as shown in formula 2, and which was reported to be 20,000 times sweeter than sucrose. See U.S. Pat. Nos. 3,907,766; 3,959,245; M. Fujino et al., *Chem. Pharm. Bull.* 24:2112–2217 (1976); M. Fujino et al., *Die Naturwissenschaften* 60:351 (1973).

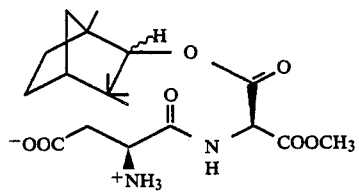

Liu Yin-Zeng, et. al., "Sino Amer. Symp. Chem. Nat. Prod.", 1980 (Beijing: Science Press 1982), pp. 254–256, have indicated that the intensity of the sweetness of compound 2 is modulated by the stereochemistry of the fenchyl group. Out of the four possible isomeric fenchyl alcohols, the pair exo/endo bearing an R configuration (chirality) at the C2 position reportedly gave rise to the highest sweetness intensity values (30,000 to 50,000×sucrose).

J. M. Janusz in EPO Appn. No. 0168112, published Jan. 15, 1986, and J. M. Gordlik in EPO Appn. No. 0168882, published Jan. 22, 1986, disclosed a series of L-aspartyl-D-phenylglycine esters having certain sweetness properties. It was found that the 2R, exo-fenchyl ester and the 2R, endofenchyl ester in this series had high sweetness intensities.

One important drawback for th applications of the fenchyl ester sweeteners like those of Liu Yin-Zeng et al. cited above, particularly in their use for soft drinks, is the release of fenchyl alcohol upon acid-catalyzed hydrolysis of the ester function. The presence of fenchyl alcohol, even at low concentrations, adversely affects the flavor characteristics of those products, due to the low taste threshold (2–5 ppm) of fenchyl alcohol and its dominant camphoraceous aroma.

The fenchyl groups of the prior art compounds are glucogenic bicycloalkyls, able to generate sweetness, but those compounds have drawbacks. Therefore, an object of the invention is the preparation of a high intensity sweetener, in which a suitable glucogenic bicycloalkyl group is attached to a dipeptide moiety in a manner which avoids the drawbacks of the prior art compounds.

SUMMARY OF THE INVENTION

This and other objects are achieved by the present invention which is directed to L-aspartyl-3-(bicycloalkyl)-L-alanine alkyl esters having high sweetness intensity. These compounds have the formula depicted below as formula 3:

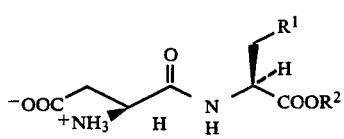

wherein $R^1$ is a substituted or an unsubstituted bicycloalkyl ring, said ring having 7 to 8 carbon atoms, the 2-position ring carbon atom is bound to the alanine moiety, the two carbon atoms of the ring that are vicinal to the 2-position carbon are each substituted by a hydrogen or lower alkyl of 1–5 carbons, the total number of alkyl groups bound to the vicinal carbons is less than three, and $R^2$ is a lower alkyl group of 1–5 carbon atoms. The bicycloalkyl ring may be substituted at positions other than said vicinal carbon by lower alkyl of 1 to 5 carbons. In preferred individual embodiments of the invention, only one of the vicinal carbons is alkyl substituted, the alkyl groups bound to the vicinal carbons have 1 to 3 carbon atoms, wherein methyl is most preferred, and the nonvicinal carbon substituents for the bicycloalkyl ring are alkyl. In a further preferred embodiment of the invention $R^2$ is methyl. All enantiomers, diastereomers and optical mixtures of the $R^1$ group are included within the invention. "2R" configuration enantiomers of the $R^1$ group are especially preferred.

In other preferred embodiments of the invention, $R^1$ is a bornyl, camphanyl, pinanyl, norbornyl, 1-methylnorbornyl, 3-methylnorbornyl, bicyclo [2.2.2] octyl, or 7,7-dimethylnorbornyl ring.

In most preferred embodiments of the invention, the $R^1$ moiety is an optical isomer or mixture of optical isomers, or has an R chiral configuration at the 2-position carbon. Examples of these most preferred embodiments include (2R)-exo norbornyl, (2R)-endo norbornyl; (1R)-exo/endo pinanyl; (2R)-exo/endo bornyl; and 2R-exo and 2R-endo 7,7-dimethylnorbornyl. Another embodiment is an edible salt of the compound of formula 3.

In another embodiment, the L-aspartyl residue of formula 3 is replaced with a 2-aminomalonic acid residue.

The invention also includes a method of using the compound of formula 3 as a high intensity sweetener, and a method of sweetening substances by adding an effective amount of the compound to an orally ingestible substance.

The compounds of the invention can be used for sweetening edible products such as foods and beverages.

DETAILED DESCRIPTION OF THE INVENTION

The 2R-endo- and 2R-exo-fenchyl esters described by Fujino, cited above, have sweetness of high intensity. However, when the non-hydrolyzable fenchyl compound of the formula 4:

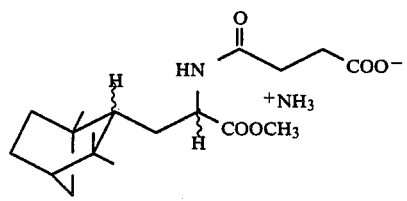

4 was prepared from fenchone, as described in the general procedure below, and then tasted in aqueous solution, it had a barely perceptible sweetness (Table I).

However, when compounds were synthesized which have the foregoing formula 3 wherein $R^1$ is a bicycloalkyl ring, and at least one of the two carbon atoms vicinal to the 2-position ring carbon bound to the alanine substituent bears a hydrogen, it was surprisingly found that they were intensely sweet. An example is the compound of formula 3 wherein $R^1$ is 3-methylnorbornyl or camphanyl. It was unexpected that elimination of one or more of the three methyls of the fenchyl group of formula 4 would produce a significant rise in sweetness potency.

Without intending to limit the scope of invention, it is hypothesized that the relief of crowding around the bicyclic C2 bearing the alanine substituent, either by removing the angular methyl group (fenchyl to camphanyl) or the gem-dimethyl groups (fenchyl to 1-methylnorbornyl), or by shifting the gem-dimethyl groups from C3 to C7 (fenchyl to bornyl), results in the manifestation of the significant sweetness found according to the invention. Table I presents a summary of these results.

In Table I, the reported sweetness is measured for diastereomeric mixtures. The sweetness of each optically pure compound according to the invention will differ from the sweetness of the mixture.

TABLE I

Sweetness of Novel L-aspartyl-3-(bicycloalkyl) D,L-alanine methyl esters

| R | Number of isomers | Sweetness (x sucrose w/w) |
|---|---|---|
| 2R—exofenchyl 2S—endofenchyl | 4 | 20 |
| norbornyl | 8 | 225 |
| 3-methylnorbornyl | 8 | 250 |
| camphanyl | 8 | 300 |
| bicyclo[2.2.2]octyl | 4 | 340 |
| bornyl | 8 | 810 |
| 1-methylnorbornyl | 8 | 450 |
| (R,S)—exo norbornyl | 4 | 200 |
| (R,S)—endo norbornyl | 4 | 290 |

TABLE I-continued
Sweetness of Novel L-aspartyl-3-(bicycloalkyl) D,L-alanine methyl esters

| R | Number of isomers | Sweetness (x sucrose w/w) |
|---|---|---|
| (1R)—exo/endo pinanyl | 4 | 160 |
| 2R—exo/2S—endo 7,7-dimethylnorbornyl | 4 | 900 |

The new sweeteners of this invention are characterized by the presence of a bicyclo [2.2.1] heptyl, a bicyclo [3.1.1] heptyl or a bicyclo [2.2.2] octyl substituent attached to the C3 of L-alanine in the dipeptide L-asp-L-ala(OCH$_3$). The alkyl substitution at the secondary and/or tertiary carbons of the bicyclic substituent usually increases the sweetness intensity of the basic structure, provided that the broader pattern of substitution is such that only one of the two carbons adjacent (vicinal) to the 2-position carbon time.

The sweetness values of each compound shown in Table I correspond to a mixture of optical isomers, whose maximum theoretical number of isomers is listed. In order to evaluate the sweetness of different isomeric forms, four pairs of optical isomers of one of the novel compounds were synthesized. Each pair differed from the others only in the stereochemistry of the bicyclic camphor ring. The sweetness of those compounds relative to sucrose is set forth in Table II.

The preferred compounds of the present invention are those enantiomers wherein R$^1$ has "R" configuration at the carbon 2 position of the bicyclic ring, because they are intensely sweet. Optically pure compounds will have sweetness differing accordingly from the results presented in Table II.

TABLE II
Sweetness of the four bornyl stereoisomers of L-aspartyl-3-bornyl-D,L-alanine methyl esters

| R | Numbers of isomers | Sweetness (x sucrose w/w) |
|---|---|---|
| 2R—exobornyl | 2 | 1690 |
| 2S—endobornyl | 2 | 70 |
| 2S—exobornyl | 2 | 350 |
| 2R—endobornyl | 2 | 1930 |

Persons skilled in the art understand that the structure shown in formula 3 is a dipeptide containing L amino acid moieties and both optically active centers in the dipeptide moiety have configuration S. The zwitterionic charge of the compound would vary according to pH, as is known to persons having skill in the art.

Further, the L-aspartic acid residue of formula 3 can be effectively replaced by a 2-aminomalonic acid residue to form intensely sweet (alpha-carboxy) glycyl-3-(bicycloalkyl)-L-alanine alkyl esters of the invention.

The sweeteners of this invention may be used to provide desirable properties of sweetness in any orally ingestable product. The sweeteners could be used in beverages such as fruit juices or drinks or carbonated soft drinks, in frozen desserts, jellies, chewing gum, dentifrices, medications or any other orally ingestible substance. The sweeteners of this invention are sweeter than sucrose, less caloric, and less likely to cause dental caries.

The sweeteners of this invention may also be blended with other sweeteners known to the art. They can be used in the form of edible salts of the compound of formula 3. Examples of such salts include sulfates, malates, carbonates, phosphates, citrates, benzoates and the like.

The present invention is illustrated by the following examples.

General Procedure for Synthesis of alpha-L-aspartyl-D,L-bicycloalkyl alanine methyl ester The intensely sweet alpha-L-aspartyl-D,L-bicycloalkyl-3-alanine methyl esters of the invention may be synthesized by the following general reaction pathway:

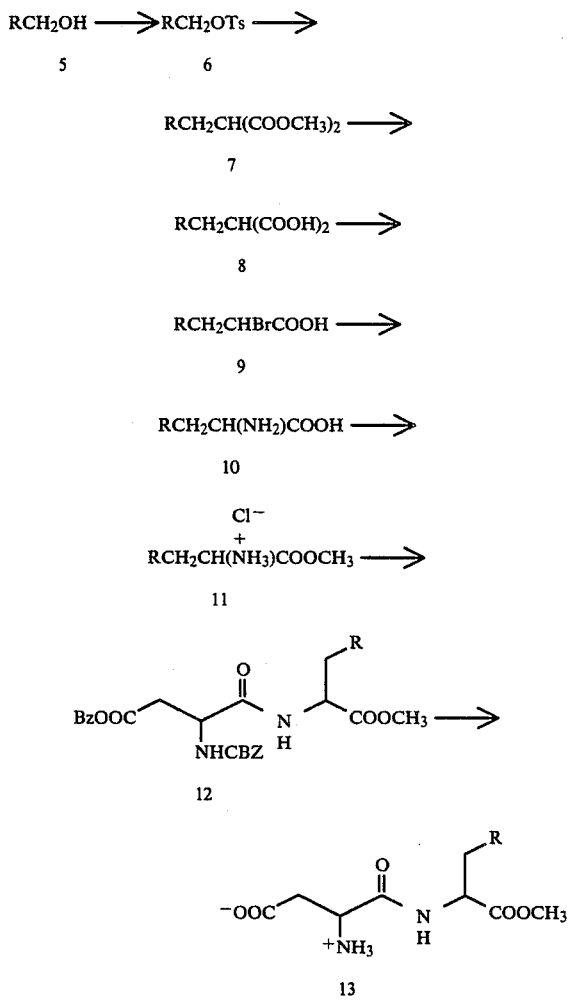

In the first step the bicyclic methanol of formula 5 is reacted with an agent which will form a facile leaving group on the hydroxy of the bicyclic methanol. Examples are tosyl, brosyl, mesyl and the like. Thus, the compound of formula 5 can be tosylated using p-toluenesulfonyl chloride/pyridine. In the second step the tosylate or other derivative of formula 6 is displaced by the anion of dimethylmalonate. In the third step the diester of formula 7 is hydrolyzed and following acidification the corresponding diacid of formula 8 is obtained.

In the fourth step, the diacid is halogenated, e.g., chlorinated, iodinated or preferably brominated, followed by heating to decarboxylate the diacid. In the fifth step, the haloacid, e.g. bromoacid of formula 9 is converted to the amino acid of formula 10 by treatment with aqueous ammonia. In the sixth step, this amino acid is esterified by treatment with methanolic hydrochloric acid giving the amino ester hydrochloride of formula 11.

In the seventh step the amino ester formula 11 is coupled to N-carbobenzyloxy-L-aspartic acid-beta-benzyl ester by the mixed anhydride method or by any other appropriate peptide formation procedure such as those utilizing carbodiimide, acid chloride, pivaloyloxy and the like, to give the protected dipeptide methyl ester of formula 12. In the last step the protecting groups are removed by hydrogenolysis using a palladium catalyst to give the sweet compound formula 13.

The bicyclic methanols of formula 5 may be obtained either from commercial sources or various synthetic sequences known to the art. These starting alcohols may contain several asymmetric centers which will result in the preparation of a final sweetener of formula 13 which contains a number of stereoisomers.

Precursors to the alcohols of formula 5, like the corresponding exocyclic olefins $R=CH_2$, can also be used as intermediates for the elaboration of the amino acid side chain. The hydroboration of such olefins with the sterically hindered hydroborating reagent 9-borabicyclo [3.3.1] nonane (9-BBN) is expected to give the tri-coordinate boron adduct, an intermediate that can be condensed with acetoxyimino glycines (M. J. O'Donnell and J. B. Falmagne, *J. Chem. Soc. Chem. Commun.* 1985, 1168–69) to yield the intermediate of formula 11 after acid workup.

It is known that the L-aspartic acid moiety of L-aspartylphenylalanine methyl ester can be effectively substituted by a 2-aminonalonic acid residue to produce sweet (alpha-carboxy) glycyl dipeptide derivatives. Briggs et al., Great Britain Pat. No. 1,299,265. In accordance with this invention, substituted or unsubstituted bicycloalkyl rings having 7 to 8 carbon atoms can be employed as the R group bound to the alanine moiety, such as bornyl, camphanyl, pinanyl, 1-methylnorbornyl, 3-methylnorbornyl, 7,7-dimethylnorbornyl, and bicyclo [2.2.2] octyl to form (alpha-carboxy) glycyl-3-(bicycloalkyl)-L-alanine methyl ester. The R chiral configuration at the 2-position carbon of the bicycloalkyl ring is preferred. Also, a lower alkyl ester may replace the methyl ester of the above compound. The characteristics of these (alpha-carboxy) glycyl compounds are similar to the characteristics of the corresponding L-aspartyl compounds of the invention.

These compounds can be conveniently prepared by reacting equivalent amounts of N-carbobenzoxy-DL-amino malonic acid monobenzyl ester with a selected amino ester of structure 11 (in the form of free base), for example, 3-norbornyl-DL-alanine methyl ester (formula 11. R=norbornyl), dissolved in anhydrous dioxane in the presence of one equivalent of N,N-dicyclohexylcarbodiimide and one equivalent of N-hydroxy-5-norbornene-2,3-dicarboximide. The reaction mixture is allowed to stand at room temperature for 18 hrs., and then filtered. The filtrate is evaporated and the resulting residue is dissolved in ethyl acetate, successively washed with 1N aqueous potassium bicarbonate, water, 0.2N citric acid, water, then dried over anhydrous sodium sulfate and evaporated. The resulting N-carbobenzoxy (alpha-benzyloxycarbonyl) glycyl-3-norbornylalanine methyl ester is dissolved in methanol, and is shaken under hydrogen in the presence of 5% palladium on carbon catalyst, at 40 psi pressure and room temperature for six hours, and then is filtered over celite. The filtrate is evaporated in vacuo at 15° C., and the resulting residue is dissolved in water, the solution filtered and then freeze-dried to yield an intensely sweet white powder, a mixture of LL, LD, DL, and DD diastereoisomers of (alpha-carboxy) glycyl-3-norbornylalanine methyl ester. Synthetic methods analogous to the foregoing which are known to those of skill in the art can also be used to prepare these (alpha-carboxy) glycyl dipeptide derivatives.

This sweet dipeptide is useful as a sweetening agent for food and pharmaceutical products, like the L-aspartyl-3-(bicycloalkyl)-L-alanine alkyl esters of the invention.

EXAMPLE 1

Synthesis of L-Asp-D,L-endo-R,S-norbornvl-3-alanine methyl ester

Step 1: Endo-R,S-norbornylmethyl tosylate.

To 22.0 g of R,S-norbornylmethanol (approx. 10:1 endo/exo) was added 150 mL pyridine and the solution cooled to 0° C. under $N_2$. 50 g of tosylchloride was added, the mixture allowed to warm to room temperature and then stirred overnight. The mixture was concentrated under reduced pressure and 1L ice water added to the residue. This solution was adjusted to pH 2 using 6N HCl and then extracted with 2×500 mL ethyl acetate. The combined organic layers were washed with 2×250 mL N HCl; 2×250 mL saturated $NaHCO_3$; 100 mL saturated NaCl and then dried over $MgSO_4$. Removal of the solvent gave an amorphous solid which was recrystallized from hexane. Yield 43.7 g. m.p. 42°–3° C.

Step 2: Dimethyl (endo-R,S-norbornylmethyl) malonate.

To a solution of 16 g of sodium in 500 mL methanol was added 150 g of dimethylmalonate. This was refluxed for 2 hours and then a solution of 43.2 g of endo-R,S-norbornyl methyl tosylate in 500 mL methanol added and the reflux continued under $N_2$. After 2 days the mixture was cooled, concentrated to half-volume and taken up in 1L ice water and 500 mL methylene chloride. After extraction with an additional 2×400 mL methylene chloride the combined organic layers were washed with 500 mL $H_2O$ and dried over $MgSO_4$. The solvent was evaporated and the residue distilled in vacuo. Following the removal of unreacted dimethylmalonate the product was distilled using a short path still head, b.p. 85°–87° C. (0.03 mm). Yield 21.0 g.

Step 3: Endo-R,S-norbornylmethylmalonic acid.

To a solution of 21.0 g of dimethyl (endo-R,S-norbornylmethyl) malonate in 50 mL methanol was added a solution of 20 g of KOH in 80 mL $H_2O$ and 160 mL methanol. This was refluxed for 6 hours and then cooled and concentrated to half-volume. 500 mL ice water was added and the aqueous solution washed with 2×200 mL ether. It was then cooled in an ice bath and adjusted to pH 2 using 6N HCl. This mixture was extracted by 4×300 mL ether, the combined organic layers washed with 100 mL saturated NaCl and dried over $Na_2SO_4$. The solvent was evaporated and the residue dried in vacuo overnight to give the diacid. Yield 12.7 g.

Step 4: 2-Bromo-3-(endo-R,S-norbornyl) propionic acid.

To a solution of 12.7 g of endo-R,S-norbornylmethyl malonic acid in 50 mL ether was added 3.2 mL bromine, dropwise, under $N_2$. After stirring for 30 minutes, 10 mL $H_2O$ was added and the stirring continued for an additional 30 minutes. The water was separated and the ether solution concentrated under reduced pressure. The residue was heated to reflux (bath temperature 140°–150° C.) for 5 hours and then distilled in vacuo, using a short path still head; b.p. 117°–120° C. (0.1 mm). Yield 13.1 g.

Step 5: D,L-(Endo-R,S-norbornyl)-3-alanine.

To 13.1 g of 2-bromo-3-(endo-R,S-norbornyl) propionic acid was added 150 mL $NH_4OH$. This mixture was stoppered and stirred for 7 days at room temperature. It was then diluted to 500 mL with water and heated overnight on a steam bath. It was cooled, filtered and the filtrate concentrated and filtered again. The combined solids were recrystallized from water. Yield 5.4 g. m. p. 248°–249° C.

Step 6: D,L-(Endo-R,S-norbornyl)-3-alanine methyl ester hydrochloride.

To 200 mL of methanolic HCl (from 10 mL of acetyl chloride) was added 5.0 g of D,L-(endo-R,S-norbornyl)-3-alanine. This solution was refluxed for 15 hours under $N_2$. It was then cooled, concentrated under reduced pressure and co-evaporated with 3×50 mL methanol. The residue was dried in vacuo giving 7.7 g of an amorphous solid. This was taken up in 50 mL of hot acetonitrile, filtered while hot and the filtrate cooled in the freezer. This gives a product which is hygroscopic. Yield 5.4 g.

Step 7: N-Carbobenzyloxy-beta-benzyl-L-aspartyl-D,L-(endo-R,S-norbornyl)-3-alanine methyl ester.

5.4 g of N-carbobenzyloxy-L-aspartic acid-beta-benzyl ester was dissolved in 200 mL tetrahydrofuran and cooled to −20° C. under $N_2$. To this was added 2.1 mL of 4-methylmorpholine and 2.4 mL i-butylchloroformate and the mixture stirred for 40 minutes at −20° C. To this was added a solution of 3.3 g of D,L-(endo-R,S-norbornyl)-3-alanine methyl ester hydrochloride in 70 mL of a 7:3 dioxane/water mixture to which 2.1 mL of triethylamine had been added. The mixture was allowed to warm to room temperature and stirred overnight. It was then concentrated, 100 mL $H_2O$ added and extracted using 3×200 mL ether. The combined organic layers were washed with 2×100 mL 5% citric acid, 2×100 mL saturated $NaHCO_3$, saturated NaCl and dried over $MgSO_4$. The solvent was evaporated leaving a clear oil that was purified by chromatography on silica gel (hexane/EtOAc). Yield 6.9 g.

Step 8: L-Aspartyl-D,L-(endo-R,S-norbornyl)-3-alanine methyl ester.

6.8 g of N-carbobenzyloxy-beta-benzyl-L-aspartyl-D,L-(endo-R,S-norbornyl)-3-alanine methyl ester was dissolved in 200 mL methanol and 0.6 g of 10% Pd/C added. This was reduced using a Parr pressure reaction apparatus at a $H_2$ pressure of 40 psig. Upon completion of $H_2$ uptake the catalyst was removed by filtration through a short pad of celite and the filtrate concentrated under reduced pressure. The residue was taken up in 400 mL $H_2O$ and freeze-dried to give a fluffy, white powder, which was in turn recrystallized from water (pH 4)/charcoal. Yield 3.0 g.

EXAMPLE 2

Cola Beverage

L-Aspartyl-D,L-(endo-R,S-norbornyl)-3-alanine methyl ester (1.5 g) is dissolved in 500 ml of water and the volume adjusted to one liter. Citric acid (1 g), phosphoric acid (2 g), caramel color (10 g), cola flavoring (10 g), and a benzoate preservative (2 g) are dissolved in the liter solution of sweetener. The resulting cola concentrate is diluted with 3 liters of water to provide a single strength beverage. Carbonation produces a satisfying effervescent carbonated cola drink.

EXAMPLE 3

Citrus Beverage 1.5 g of L-aspartyl-D,L-(endo-R,S-norbornyl)-3-alanine methyl ester is dissolved in 1 liter of water. To this, 4.5 g citric acid, 2 g of sodium benzoate and 10 g of citrus flavoring are added. The resulting citrus concentrate is diluted with 3 liters of water to provide a single strength beverage Carbonation as desired gives a satisfactory effervescent beverage having a palatable sweetness.

We claim:

1. An intensely sweet compound of the formula:

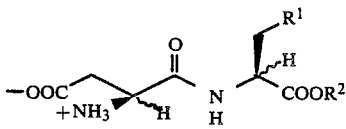

wherein $R^1$ is a bicycloalkyl ring, said ring having 7 to 8 carbon atoms, the 2-position ring carbon atom is bound to the alanine moiety, and the two carbon atoms of the ring vicinal to said 2-position carbon are each substituted by a hydrogen or lower alkyl of 1-5 carbons, the total number of alkyl groups bound to the vicinal carbons is less than three, and $R^2$ is a lower alkyl group of 1-5 carbons; and edible salts thereof.

2. A compound according to claim 1, wherein only one of the vicinal carbons is alkyl substituted.

3. A compound according to claim 1 wherein the alkyl groups bound to the vicinal carbons have 1-3 carbon atoms.

4. A compound according to claim 1, wherein the alkyl bound to the vicinal carbons is methyl.

5. A compound according to claim 1 wherein $R^2$ is methyl.

6. A compound according to claim 1, wherein the ring is selected from the group consisting of camphanyl, norbornyl, 3-methylnorbornyl, 1-methylnorbornyl, and bicyclo [2.2.2] octyl.

7. A compound according to claim 1, wherein $R^1$ is (2R)-exo norbornyl.

8. A compound according to claim 1, wherein $R^1$ is (2R)-endo norbornyl.

9. A method of sweetening substances comprising adding an effective amount of the compound of claim 1 to an orally ingestible substance.

10. A sweetened food product containing the compound of claim 1.

11. A sweetened beverage containing the compound of claim 1.

12. A compound according to claim 1 wherein the $R^1$ moiety is an optical isomer or mixture of optical isomers.

13. A compound according to claim 1 wherein the $R^1$ moiety has an R chiral configuration at the 2-position carbon.

14. A compound according to claim 6 wherein the $R^1$ moiety has an R chiral configuration at the 2-position carbon.

15. A compound according to claim 1, wherein at least one bicycloalkyl ring nonvicinal carbon is alkyl-substituted by lower alkyl of one to five carbons.

16. A compound according to claim 15, wherein the ring is selected from the group consisting of bornyl and pinanyl.

17. A compound according to claim 15, wherein $R^1$ is (1R)-exo pinanyl.

18. A compound according to claim 15, wherein $R^1$ is (2R)-exo bornyl.

19. A compound according to claim 15, wheren $R^1$ is (2R)-endo bornyl.

20. A compound according to claim 15, wherein $R^1$ is (2R)-exo 7,7-dimethylnorbornyl.

21. A compound according to claim 15, wherein $R^1$ is (2R)-endo 7,7-dimethylnorbornyl.

22. An intensely sweet compound of the formula:

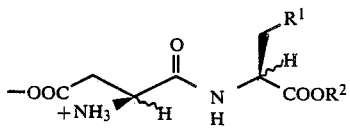

wherein $R^1$ is a 7,7-dimethylnorbornyl ring, the 2-position ring carbon atom is bound to the alanine moiety, and the two carbon atoms of the ring vicinal to said 2-position carbon are each substituted by a hydrogen or lower alkyl of 1-5 carbons, the total number of alkyl groups bound to the vicinal carbons is less than three, and $R^2$ is a lower alkyl group of 1-5 carbons; and edible salts thereof.

* * * * *